(12) United States Patent
Cobham (10) Patent No.: US 8,765,267 B2
(45) Date of Patent: Jul. 1, 2014

(54) COMPOSITION AND METHOD FOR TREATING WOOD

(75) Inventor: Peter Raynor Soundy Cobham, Pelican Waters (AU)

(73) Assignee: Danip Pty Ltd, Maroochydore, Queensland (AU)

( * ) Notice: Subject to any disclaimer, the term of this patent is extended or adjusted under 35 U.S.C. 154(b) by 0 days.

(21) Appl. No.: 13/380,242

(22) PCT Filed: Jun. 23, 2010

(86) PCT No.: PCT/AU2010/000793
§ 371 (c)(1),
(2), (4) Date: Feb. 24, 2012

(87) PCT Pub. No.: WO2010/148450
PCT Pub. Date: Dec. 29, 2010

(65) Prior Publication Data
US 2012/0148859 A1  Jun. 14, 2012

(30) Foreign Application Priority Data
Jun. 23, 2009 (AU) .................................. 2009902894

(51) Int. Cl.
*B32B 5/16* (2006.01)
(52) U.S. Cl.
USPC ................ 428/537.1; 428/402.2; 427/393; 427/397; 106/15.05
(58) Field of Classification Search
USPC .................. 428/537.1, 402.2; 427/393, 397; 106/15.05
See application file for complete search history.

(56) References Cited

U.S. PATENT DOCUMENTS

| | | | | |
|---|---|---|---|---|
| 5,407,920 A | * | 4/1995 | Dawson | 514/65 |
| 5,444,078 A | * | 8/1995 | Yu et al. | 514/372 |
| 5,582,869 A | * | 12/1996 | Yu | 427/297 |
| 6,235,403 B1 | * | 5/2001 | Vinden et al. | 428/537.1 |
| 7,297,193 B1 | | 11/2007 | Ashmore et al. | |
| 7,361,215 B2 | * | 4/2008 | Cobham | 106/18 |
| 7,625,577 B2 | * | 12/2009 | Cobham | 424/409 |

FOREIGN PATENT DOCUMENTS

| | | |
|---|---|---|
| WO | WO 93/14630 | 8/1993 |
| WO | WO93/14630 * | 8/1993 |
| WO | WO 99/55505 | 11/1999 |
| WO | WO99/55505 * | 11/1999 |

OTHER PUBLICATIONS

International Search Report, International Application No. PCT/AU2010/000793, Dated: Aug. 19, 2010.
International Preliminary Report on Patentability, International Application No. PCT/AU2010/000793, Dated: Jan. 4, 2012.

* cited by examiner

*Primary Examiner* — Leszek Kiliman
(74) *Attorney, Agent, or Firm* — Hamilton, Brook, Smith & Reynolds, P.C.

(57) ABSTRACT

The invention relates to a composition for treating wood comprising at least one wood preserving compound and a carrier, wherein said carrier is an emulsion or microemulsion having a water to oil ratio of greater than 30 up to 92.5 water to 7.5 to less than 70 oil, wherein the oil has a flash point above 61° C. The invention also relates to methods of treating wood with the composition.

20 Claims, 6 Drawing Sheets

COMPOSITION AND METHOD FOR TREATING WOOD

This application is the U.S. National Stage of International Application No. PCT/AU2010/000793, filed Jun. 23, 2010, which designates the U.S., published in English, and claims priority under 35 U.S.C. §§119 or 365(c) to Australian Application No. 2009902894, filed Jun. 23, 2009.

FIELD OF THE INVENTION

The present invention relates to a composition for treating wood comprising a wood preserver and a carrier, wherein the carrier is an emulsion or microemulsion. Methods of treating wood with the composition are also described.

BACKGROUND OF THE INVENTION

Wood is a common commodity used in home building (frames and trusses), exterior construction (fencing, gazebos, trellising), indoor use (furniture, floors), in ground use (farm fencing, vineyard trellising, utility poles) and for use in marine environments (piling). Apart from naturally durable woods, all these applications require chemical protection of the wood from fungal, bacterial and insect attack, especially from termite attack.

Standards for wood protection have been developed either on a country or regional basis. These standards are subdivided into hazard classes based on the biological hazard involved and the commodity involved. For example, the Australian and New Zealand standards (AS1604 and NZS3640) provide the following Hazard classes:

Hazard Class 1: Insect Attack; wood in internal situation protected from weather.
Hazard Class 2: Termite Attack; wood in internal situation protected from weather.
Hazard Class 3: Fungal, insect and termite attack; wood in external situation above ground but subject to rain wetting.
Hazard Class 4: Fungal, bacterial, insect and termite attack; wood in ground, subject to rain wetting.
Hazard Class 5: Fungal, bacterial, insect and termite attack; wood in ground, subject to rain wetting. High hazard for utility poles etc.
Hazard Class 6: Marine organisms, fungal, bacterial, insect and termite attack in marine environment.

For each Hazard Class, the standards define retention and penetration of the wood commodity required by preservative treatment. For example, Hazard Class 3 and above will normally require at least full sapwood penetration of the preservative chemical, whereas envelope treatments are acceptable for insect and termite protection in Hazard Classes 1 and 2.

The preservative may be included in a composition containing a carrier. Carriers range from water to non-aqueous carriers such as solvents or oils depending on their boiling point range.

Wood treated with aqueous preservative compositions increase the water content of the wood and cause swelling. A typical water-borne treatment has an uptake of 300 to 600 L/m$^3$. These treatments are often referred to as providing "wet after" wood. Wet after wood will dry in service down to provide an equilibrium moisture content. In Australia and New Zealand, typical equilibrium moisture content is 15-18%. The drying of the wet after wood will subject the wood to shrinkage and checking which can affect the appearance of the timber. Furthermore, swelling or shrinkage in a wall frame or truss can lead to both structural and cosmetic defects in a building.

Non-aqueous formulations, such as Light Organic Solvent Preservatives (LOSP), provide timber that can be supplied at a moisture content equivalent to the equilibrium moisture content and are often referred to as providing "dry after" wood. A typical LOSP treatment has an uptake ranging from 30 to 50 L/m$^3$. Unlike aqueous formulations, non-aqueous formulations do not swell the wood. However, non-aqueous formulations often contain high levels of volatile organic chemicals (VOCs) that can result in release of "greenhouse gasses" and odour being associated with the treated timber. Some non-aqueous formulations although initially assisting in penetration of the preserving agent into the wood can subsequently cause the preserving agent to bleed to the surface of the wood where it is then lost. Non-aqueous treatments, although not swelling the treated wood, are significantly more expensive than aqueous treatments.

Another problem with non-aqueous treatment occurs when the wood to be treated is infected with fungi causing, for example, "blue stain" or sapstain. In such infected wood, there is discolouration of the wood. Although the fungal infection does not adversely affect the strength of the wood, the infection causes rapid and uncontrolled uptake of non-aqueous preservative compositions into the wood. This is a real economic problem, particularly with expensive non-aqueous formulations used for dipping methods.

"Dry after" wood can also be achieved by redrying wood that has been water-borne treated but this is expensive and can result in timber degradation due to splitting and dimensional movement.

Some aqueous/glycol formulations can be used to form envelopes. However, these compositions are fundamentally polar and result in swelling of the wood.

Furthermore, neither aqueous nor non-aqueous formulations available allow control of penetration of the preserving agent to obtain an envelope of specific depth.

There is a need for new wood preserving formulations that allow controlled penetration of the preserving agent, do not result in a swelling of the wood or bleeding/leaching of the preservative and are more economical than formulations currently available.

SUMMARY OF THE INVENTION

The present invention is predicated in part on the fact that emulsions and microemulsions could be used as suitable carriers for treating wood with a wood preservative without reducing high preservative retention but with little increase in moisture content of the wood therefore little or no swelling. Such formulations may also reduce the costs associated with non-aqueous formulations. Furthermore, low uptake of the formulation, typically associated with LOSP treatment, for example 30 to 50 L/m$^3$, has also been found to give the required penetration and retention when using the emulsion or microemulsion of the invention.

In a first aspect of the present invention there is provided a composition comprising at least one wood preserving compound and a carrier, wherein said carrier is an emulsion or microemulsion having a water to oil ratio of:
 greater than 30 up to 92.5 water:7.5 to less than 70 oil;
 wherein the oil has a flash point above 61° C.

In some embodiments, the ratio of water and oil in the emulsion or microemulsion is greater than 30 to 90 water: 10 to less than 70 oil or 45 to 80 water:20 to 55 oil, especially 50 to 75 water:25 to 50 oil. In some embodiments, the oil is a mineral oil, a vegetable oil, biodiesel, an aromatic solvent, aromatic oil or mixtures thereof, especially narrow cut kerosene, high flash kerosene, biodiesel or iso-paraffinic solvents. In some embodiments, the preservative compound is a fungicide, insecticide, termiticide or bactericide, especially a termiticide. In some embodiments, the emulsion or microemulsion further comprises a surfactant, especially a surfactant having an HLB between 4 and 12.

In another aspect of the invention, there is provided a method of treating wood comprising the steps of:
providing wood to be treated;
contacting the wood to a composition of the invention.

In some embodiments, the wood is timber or an engineered wood product. In some embodiments the wood is contacted with the composition by dipping (individual piece or strapped packs), spraying, rolling, misting or brushing. In other embodiments, the wood is contacted with the composition by a vacuum pressure process. In some embodiments, the uptake of the composition of the invention (irrespective of application method) is also unaffected by fungal infection such as blue stain or sapstain.

In another aspect of the invention there is provided wood or engineered wood products treated by the method outlined above.

DESCRIPTION OF THE INVENTION

The present invention seeks to reduce the cost of the carrier required in wood treatment compositions while not substantially increasing swelling of the wood and without substantially reducing retention of the preservative by the wood. Advantageously, the present invention may also allow control of the size of the envelope formed upon treatment. Thus the present invention provides an alternative wood preserving composition and method to those currently available.

The oil used to form the carrier emulsion or microemulsion is a combustible oil having a flash point of 61° C. and above. The oil used in the present invention is not a flammable oil. The University of Queensland guidelines for handling and storage of flammable and combustible liquids (http://www.u-q.edu.au/hupp/Index.html?page=250428pid=25039) separates combustible oils into two classes, those with a flash point between 61° C. and 150° C. and those having a flash point above 150° C. In contrast flammable liquids have flash points below 61° C. In some embodiments the oil is selected from mineral oils, vegetable oils, fish oils, biodiesel, aromatic solvents, aromatic oil and mixtures thereof. The biodiesel may be sourced from edible or non-edible sources including vegetable oils, animal fat or alcohol. Suitable aromatic solvents include naphthalene and indene and aromatic oil is a mixture of naphthalene, 3a,4,7,7a-tetrahydro-4,7-methanoindene and optionally indene. In particular embodiments the oil is paraffin oil, isoparaffin oil, such as Isopar L, M or V, narrow cut kerosene, high flash kerosene or biodiesel sourced from non-edible vegetable oils. If a mixture of oils is used in the emulsion or microemulsion, the mixture must be combustible and have a flash point of 61° C. or above. In some embodiments, the oil is not a mixture of a drying oil such as linseed oil or fish oil and an extender oil such as heating oil.

In some embodiments the oil has a low level of volatile organic compounds (VOCs) and is therefore odourless or substantially odourless and has limited impact on "greenhouse gas" release.

The water and oil content is provided as a ratio of oil and water in the emulsion or microemulsion. The water is present in an amount greater than 30% up to 92.5% v/v of the mixture of oil and water. The oil is present in an amount from 7.5% to less than 70% v/v of the mixture of oil and water. In some embodiments, the ratio of water is greater than 30% up to 90% v/v, 45 to 80% v/v, especially 50 to 75% v/v of the mixture of oil and water. In these embodiments, the ratio of oil in the mixture of oil and water is 10 to less than 70%, 20 to 55% v/v especially 25 to 50% v/v.

In some embodiments, the ratio of water and oil in the mixture is selected to achieve a particular size of envelope. For example, a ratio of 25:75 v/v oil:water may be selected to provide a 3 mm envelope or a ratio of 50:50 v/v oil:water may be selected to provide a 5 mm envelope. Different envelope sizes may be obtained by varying the ratio of water to oil. Particular treatments providing 3 mm to 5 mm envelopes may be suitable for wood treatment in Hazard classes 1 and 2.

As used herein the term "envelope" refers to where treated wood has absorbed the composition radially, tangentially and/or longitudinally to a depth from the surface of the wood. Controlled envelope formation refers to where the composition is absorbed into the wood substantially evenly in the radial and tangential direction. In some embodiments, the depth of the envelope may be predicted from the ratio of oil and water in the emulsion or microemulsion. In some embodiments, the composition may be absorbed rapidly on a radially cut face and less rapidly on a tangentially cut face resulting in an envelope of uneven depth. The depth of the envelope achieved may also be affected by the quality and/or type of wood being treated.

A wide variety of preservatives can be included in the composition of the invention. Oil soluble preservatives are contained in the oil phase of the emulsion or microemulsion. Water soluble preservatives are contained in the water phase of the emulsion or microemulsion. The preservative may be any preservative that is required to protect wood from biological organisms. For example, the preservative may be a fungicide, bactericide, insecticide or a termiticide. Suitable insecticides and termiticides include synthetic pyrethroids such as permethrin, cypermethryn, deltamethrin, and bifenthrin and neonicotinoids such as imidichloprid and thiochloprid. Suitable fungicides and mouldicides include creosote, pentachlorophenol (PCP), azoles such as tebcuconazole, propiconazole, cyperconazole and the like; organic copper compounds such as copper 8-quinolinolate, copper naphthenate and bis-(N-cyclohexyldiazeniumdioxy)copper (Cu-HDO), organic zinc compounds such as zinc naphthenate, organic tin compounds such as tributyl-tin naphthenate (TBTN); silver compounds, iodopropynyl-butylcarbamate (IPBC), 3-benzothien-2-yl-5,6dihydro-1,4,2-oxathiazine-4-oxide (Bethoguard®), quaternary ammonium compounds, tertiary ammonium compounds and isothiazalones and boron compounds. The preservatives may also be a micronised or dispersed active such as copper carbonate, copper oxide, or oxine copper.

In some embodiments, the composition may comprise a mixture of preservatives. For example, fungicides such as propiconizole and tebuconizole may be used together in a 1:1 ratio. Suitable amounts of these compounds may achieve a timber loading of 0.03% mass/mass for each compound. In other embodiments, the composition may contain fungicides and insecticides or termiticides. For example, a combination of propiconizole and tebuconizole may be combined with a pyrethroid such as bifenthrin or permethrin. Suitable ratios would be 1 (propiconizole):1 (tebuconizole):0.67 (permethrin) or 0.16 (bifenthrin). A suitable combination would be propiconizole and permethrin or bifenthrin. A person skilled in the art could determine suitable amounts of fungicides or insecticides to use in a mixture to achieve a desired % mass/mass loading in the timber product.

In some embodiments, the wood preserving compound is solubilised in the oil or water phase. In other embodiments, the wood preserving compound may be encapsulated and solubilised or suspended in the oil or water phase. Encapsulation may be particularly useful if the preservative is toxic to humans, heat unstable and/or chemically unstable in water or oil or if a slow release of the preservative is required. Microencapsulation of the preservative may be achieved by methods known in the art, such as pan coating, air-suspension coating, centrifugal extrusion, vibration nozzle encapsulation, spray drying, interfacial polymerization, in-situ polymerisation and matrix polymerisation.

The amount of preservative present in the composition is dependent on the type of preservative used and the loading required. A person skilled in the art could readily determine a suitable amount of preservative. In general, the preservative will be included in an amount of below 10% of the composition, especially below 5% of the composition, more especially below 2% of the composition.

In some embodiments, the composition further comprises a surfactant or emulsifier to stabilise the emulsion or microemulsion of oil and water. Suitable surfactants or mixtures of surfactants have an HLB value of between 4 and 12. In some embodiments when the emulsion or microemulsion is an oil-in-water emulsion or microemulsion, the surfactant or surfactant mixture has an HLB of 8 to 12. In some embodiments, when the emulsion or microemulsion is an water-in-oil emulsion or microemulsion, the surfactant or mixture of surfactants has an HLB of 4 to 6. The surfactants can be nonionic, anionic or cationic surfactants, especially nonionic surfactants. Suitable surfactants include nonylphenol alkoxylates, ethoxylated caster oils, alcohol alkoxylates, tristyrolphenols, anionic/nonionic blends, alkylamine ethoxylates, sorbitan esters, surfactants sold under the tradename Tersperse®, such as Tersperse® 4896 (a nonionic wetter and dispersant) Tersperse® 4890 (a polymeric amine condensate) and Tersperse® 2500 (an acrylic graft copolymer surfactant), that have low HLB values suitable for emulsifying water in oil emulsions and microemulsions, Termul® emulsifiers such as Termul® 200, 5360, 5370, 5600, 7220, 1283, 1284, 1285, 2507, 3512, 3540, 203, 5429, 5500, 7240, 3130, 3140, 3150, 3162, 3170, 3180, 3190, 3194, 3195, 3196, 5030, 5101 and 5123, which are all suitable for emulsifying oil in water emulsions and microemulsions, Teric® alkylamine 17M2 (HLB 9, Teric® 17M5 (HLB 10), Teric® 18M2 (HLB 8.5), Teric® 18M5 (HLB 9.5), Teric® 18M10 (HLB 11.2), Teric® 12A2C (HLB 6.0) and Teric® 12A1N (HLB 3.6), Sorbitan monooleate (Span 80, HLB 4.3), Sorbitan monostearate (Span 60, HLB 4.7), Sorbitan monopalmitate (Span 40, HLB 6.7), Sorbitan monolavrate (Span 20, HLB 8.6), polyoxyethylene sorbitan tristearate (Tween 65, HLB 10.5) and polyoxyethylene sorbitan trioleate (Tween 85, HLB 11.0). A person skilled in the art could determine suitable surfactants or emulsifiers for oil-in-water or water-in-oil emulsions and microemulsions.

The surfactant or emulsifier is added in the composition in an amount that results in emulsification of the oil and water to form a stable emulsion or microemulsion. In general, the emulsifier or combination of emulsifiers will be included in an amount of below 10% of the composition, especially below 2% of the composition, more especially below 1% of the composition.

The composition may also include other optional components such as corrosion inhibitors, colouring agents such as dyes or pigments, for example, a blue dye to indicate that the wood has been treated, water repellents such as waxes, resins, fire retardants, UV stabilisers, adjuvants and algicides.

One advantage of the present invention is that although there is significant water in the composition, the oil phase of the emulsion or microemulsion remains mobile in the wood and therefore can provide a self healing effect. This is particularly advantageous when the preservative is soluble in the oil phase. When the oil phase is mobile in the wood and the preservative is present in the oil phase, after formation of the initial envelope, if the wood is cut to expose fresh wood surface, the oil phase containing the preservative will migrate longitudinally to the freshly cut surface and then move tangentially and radially across the cut surface providing preservative protection to that surface. This enables maintenance of the treatment envelope upon cutting of the wood. It is believed that this self healing effect will be maintained for about 1-2 weeks up to several months, depending on the boiling point of the non-aqueous phase of the emulsion or microemulsion.

The envelope may be formed with both heartwood and sapwood.

In some embodiments, the composition comprises an emulsion. An emulsion comprises two immiscible liquids, one liquid forming the carrier phase and one liquid forming the dispersed phase. The dispersed phase is dispersed as particles or droplets in the carrier phase. Emulsions tend to be cloudy as the phase interfaces tend to scatter light. Emulsions require energy input to form through shaking, mixing, homogenising or spraying or in some cases, high shear mixing. Emulsions often have a wide range of particle or droplet sizes in the dispersed phase and the droplet size is greater than that in a microemulsion.

In some embodiments, the composition comprises a microemulsion. A microemulsion is a macroscopically homogenous mixture of oil, water and optionally, surfactant. The particle size of the particles in a microemulsion is smaller than those in an emulsion and therefore microemulsions are often optically clear. Unlike emulsions, microemulsions can be formed upon simple mixing of the oil and water phases.

The emulsions and microemulsions are formed by mixing the oil and water phases, at least one of which comprise a preservative compound, and optionally comprising a surfactant/emulsifier. The mixing may be regular mixing or be high shear mixing as is known in the art.

In another aspect of the invention there is provided a method of treating wood comprising the steps of:
providing wood to be treated;
contacting the wood with a composition comprising at least one wood preserving compound and a carrier, wherein said carrier is an emulsion or microemulsion having a water to oil ratio of:
greater than 30 up to 92.5 water:7.5 to less than 70 oil;
wherein the oil has a flash point above 61° C.

In some embodiments the wood is timber or an engineered wood product. The timber may be timber that may be treated to provide preservative envelopes of hazard classes 1 and 2 such as timber used as building materials for trusses and frames. Treatment where full sapwood penetration and envelope penetration to the heartwood can also be achieved for higher hazard classes such as 3-5 where timber is used in an external situation. Typical uses for this timber include fencing, trellises, gazebos, and outdoor furniture. In some embodiments the wood is sapwood. In other embodiments the wood is heartwood. Suitable woods include softwoods and hardwoods. Softwoods such as *Pinus radiata*, Southern yellow pine species, *Pinus elliottii* and *Pinus sylvestris*, are typically used in house frames and trusses. Engineered wood products include wood composite materials made of wood fibres, wood particles, wood veneer, wood strands or mixtures thereof. Example of engineered wood products are plywood, laminated veneer lumber, oriented strand board, particle board and medium density fibre board.

The wood to be treated may be contacted with the composition by methods known in the art. For example in some embodiments, the wood is contacted with the composition by dipping (individual piece or strapped packs), spraying, rolling, misting or brushing. In other embodiments the wood is contacted with the composition in a vacuum pressure process.

For example, the wood may be typically contacted with the composition by dipping (individual piece or strapped packs), spraying, rolling, misting or brushing for at least about 15 to 90 seconds, for example 20 to 60 seconds. Some timber species may require a longer dip time to achieve adequate penetration and retention. The contact is then followed by draining of any excess preservative from the wood for 5 to 20 minutes, especially about 10 minutes. For spraying, rolling, misting or brushing a specific uptake of composition should be targeted, such as 5 to 20 L/m$^3$ or 10 to 20 L/m$^3$ to achieve similar penetration and retention as found with dipping.

In a particular embodiment, the wood is contacted with the composition by dipping. Dipping can be of individual pieces of wood or strapped packs of wood. This method may be particularly advantageous with strapped packs where acceptable coverage of the wood pieces in the internal part of the pack is difficult to achieve by other methods such as spraying. Dipping of strapped packs can achieve full coverage of the wood pieces in the pack, even the internal wood pieces, if the strapped pack is dipped deep enough in the immersion or dipping bath such that a hydrostatic head pressure of at least 5 kPa is exerted at the top of the pack. The required hydrostatic head pressure will depend on the strap tension of the pack. The higher the strap tension, the higher the hydrostatic head pressure required to obtain full coverage of the internal wood pieces in the strapped pack. The hydrostatic head pressure may be between 5 and 20 kPa, for example, 6 kPa, 7.5 kPa, 10 kPa, 12 kPa, 15 kPa or 20 kPa, especially at least 10 kPa.

The uptake of the composition is important to achieve a level of preservative required to achieve the results required, for example, protection against termite attack. The loading of the preservative in the timber is referred to in % mass/mass which is a percentage indicating mass of preservative in a given mass of wood. In one embodiment where the preservative is bifenthrin, the toxic threshold for termiticidal activity is 0.0004 to 0.02% mass/mass and for permethrin the uptake must provide at least 0.02% mass/mass permethrin to meet Australian Standards (AS1604).

The timber may be treated as individual pieces or in a timber pack (full pack) where a number of timber pieces are tightly strapped together ready for transport.

In some embodiments, the wood is subject to a vacuum pressure process in the presence of the composition. Vacuum pressure treatment is known in the art and may involve the use of low pressure Bethell, Lowry or Reuping process or Vac-Vac process as used with the LOSP. The vacuum pressure process is suitable for achieving full sapwood penetration of the preservative without substantially increasing the moisture content of the wood. For example, a 50:50 oil:water emulsion with an uptake of 40 Liters per cubic meter (20 L/m$^3$ water), assuming a basic wood density of 550 kgm/m$^3$, would increase the moisture content of wood by only 4%. This is in contrast to a 100% water-borne treatment where high uptake is required (>300 L/m$^3$) that could increase the moisture content of the wood by >50%. By "without substantially increasing moisture content of the wood" refers to an increase in moisture of less than 10%, especially less than 8% or 6% and especially less than 4%.

There are a number of advantages of the vacuum pressure process. In particular, replacing the low odour solvent with the emulsion or microemulsions of the invention significantly reduces cost without affecting efficacy of the treatment and with minimal effects on moisture treatment content and swelling of the wood. Furthermore, there are less volatile organic compounds present and therefore less "greenhouse gas" emissions and reduced odour. The use of a high flash point oil also provides engineering advantages as the process is significantly less flammable than LOSP.

In another aspect of the invention there is provided wood or engineered wood products treated by the method outlined above.

In order that the nature of the present invention be more clearly understood and put into practical effect, specific embodiments will now be described by way of the following non-limiting examples.

EXAMPLES

Example 1

Preparation of Emulsion

1 Liter of the chosen oil is vigorously mixed with an emulsifier, ethoxylated castor oil, (approximately 1% by weight) for 2 to 3 minutes. For a 50% v/v mix (ratio oil:water, 50:50), 1 Liter of water is slowly added with continuous vigorous stirring. Stirring continued for 5 minutes after all water had been added.

Example 2

Twelve end matched samples of *Pinus radiata* were end sealed with a silicon sealant and treated with paraffin oil (100%, emulsion of paraffin oil (25):water (75), emulsion of paraffin oil (50):water (50) or an emulsion of paraffin oil (75):water (25). Treatment was by 1 minute dip and 10 minute drain.

The average uptake of oil or emulsion in Liters/cubic meter (L/m$^3$) was assessed by weighing end seal wood samples before and after treatment. Density of the treating solution was taken into account when determining the uptake.

After treatment the wood samples were allowed to sit for 24 hours prior to cross-cutting to assess penetration. Given the potential for samples to self heal, penetration was noted within 10 minutes of cutting. After a further 24 hours self healing was noted. Thin sections could then be cut on a regular basis to monitor continued self healing.

The size of the envelope formed and the degree of self healing was measured using digital callipers.

The results are shown in Table 1.

TABLE 1

| Treatment | Ave Uptake (L/m$^3$) | Envelope (mm) | Self healing |
|---|---|---|---|
| Paraffin oil | 22.8 | >5 | Yes (complete) |
| 25% Paraffin:75% water | 20.6 | 3 | Yes |
| 50% Paraffin:50% water | 20.2 | 5 | Yes |
| 75% Paraffin:25% water | 22.1 | >5 | Yes |

As can be seen from the results, compositions containing paraffin oil only or an emulsion with a ratio of 75 oil:25 water allowed no control of the size of the envelope whereas with 50 oil:50 water a 5 mm envelope was obtained and with 25 oil:75 water a 3 mm envelope was obtained.

The increased amount of water in the emulsion did not substantially affect uptake of the oil into the wood. Furthermore, the water phase did not substantially migrate from the surface of the wood, as penetration of the water phase was 2 mm or less.

The envelope formation was almost instantaneous but the oil remained mobile in wood moving longitudinally to a cut surface and then radially and tangentially across the cut surface to provide self healing.

Example 3

Twelve end matched *Pinus radiata* wood samples were used to compare average uptake (L/m$^3$), envelope formation and self healing after treatment with an emulsion of low odour kerosene (50%) (flash point less than 61° C. and therefore flammable) and water (50%) or an emulsion of isoparaffin (flash point >64° C.) (50):water (50). Treatment was by 1 minute dip followed by 10 minute drain.

The average uptake, envelope formation and self healing were assessed in the same manner as in Example 1. The results are shown in Table 2.

TABLE 2

| Treatment | Ave Uptake (L/m$^3$) | Envelope (mm) | Self healing |
|---|---|---|---|
| 50:50 Kerosene:water | 16.1 | No | No |
| 50:50 isoparaffin:water | 23.9 | >5 | Yes |

The low flash point kerosene gave an emulsion that provided a low uptake, no envelope and no self healing. This is surprising given treatment with 100% low flash point solvents will give rapid uncontrolled penetration. It would be expected that kerosene as part of an emulsion would penetrate better than when used alone, but this is not the case. In contrast, the higher flash point (>64° C.) isoparaffin containing emulsion provided good uptake, an envelope and self healing.

Example 4

An emulsion of biodiesel and water was prepared and used to treat 12 samples of end matched wood. The dip time was varied and drain time was 10 minutes. Average uptake of the composition, uptake of oil, envelope formation and self healing was assessed. The results are shown in Table 3.

TABLE 3

| Ratio bio-diesel:water | Dip time (min) | Ave uptake (L/m$^3$) | Oil uptake (L/m$^3$) | Envelope (mm) | Self healing |
|---|---|---|---|---|---|
| 60:40 | 1 | 28.8 | 17.3 | >5 | Yes |
| 40:60 | 1 | 20.7 | 8.3 | >4 | Yes |
| 40:60 | 2 | 22.3 | 13.4 | >5 | Yes |
| 20:80 | 2 | 20.6 | 4.1 | >2 | Yes |

Self healing decreased with the ratio of biodiesel to water, for example oil:water 60:40 had more self healing than oil:water 40:60. Uptake of the composition decreased with lower oil to water ratios but this could be overcome by longer dipping time. In observing the results with the biodiesel:water 20:80 sample, it was surprising how much penetration and self healing was achieved given the low uptake of oil (4 L/m$^3$).

Example 5

In accordance with Australasian Wood Preservation Committee (AWPC) Protocols for the Assessment of Wood Preservatives, a termite field trial was carried out to prove performance of bifenthrin and permethrin in novel emulsion system. Trial was located near Townsville, Queensland Australia. Termite species of interest was *Coptotermes acinaciformis*.

Timber species treated in this trial was *Pinus elliottii* (slash pine). The trial ran for 4 months. Slash pine treated with 0.02% m/m permethrin (carrier low odour kerosene, flash point <61° C.) was included as a positive control. This loading of permethrin is in compliance to Hazard Class H2 as defined in Australian Standard (AS) 1604.1 2005.

Formulations used—
1. 60:40 emulsion water and high flash kerosene with permethrin (0.02% m/m wood loading)
2. 60:40 emulsion of water and bio-diesel with permethrin (0.02% m/m wood loading)
3. 60:40 emulsion of water and high flash kerosene with bifenthrin (0.02% m/m wood loading)
4. 60:40 emulsion of water and bio-diesel with bifenthrin (0.02% m/m wood loading)

Results were assessed by weight. Each sample was weighed before and after treatment with the formulation to assess uptake of the emulsion and then again after exposure to termites for 4 months.

The Uptakes for emulsion formulations are shown in Table 4.

TABLE 4

| Treatment | Emulsion 1 | L/m$^3$ | Emulsion 2 | L/m$^3$ |
|---|---|---|---|---|
| 0.02% m/m Permethrin | 60:40 Water:High Flash Kerosene | 36.9 | 60:40 Water:Bio-diesel | 39.9 |

TABLE 4-continued

| Treatment | Emulsion 1 | L/m³ | Emulsion 2 | L/m³ |
|---|---|---|---|---|
| 0.02% m/m Bifenthrin | 60:40 Water:High Flash Kerosene | 34.5 | 60:40 Water:Bio-diesel | 43.0 |

Results showed that while untreated control and feeder boards were significantly attacked by *Coptotermes acinaciformis* the treated samples while grazed by the termites suffered from zero weight loss.

The results were assessed with the following scale:
Pass—less than 5% weight loss
Fail—greater than 5% weight loss
Results are shown in Table 5.

TABLE 5

| Treatment | Carrier | Weight change | Grade |
|---|---|---|---|
| 0.02% m/m Permethrin | Low Odour Kerosene | 0% | Pass |
| 0.02% m/m Permethrin | 60:40 Water:High Flash Kerosene | 0% | Pass |
| 0.02% m/m Bifenthrin | 60:40 Water:High Flash Kerosene | 0% | Pass |
| 0.02% m/m Permethrin | 60:40 Water:Bio-Diesel | 0% | Pass |
| 0.02% m/m Bifenthrin | 60:40 Water:Bio-Diesel | 0% | Pass |
| Untreated | Untreated | >50% | Fail |

Conclusions

Formulations of bifenthrin and permethrin when treated in accordance with Australian Standard AS1604.1 2005 to levels required for Hazard Class H2F were not adversely affected by emulsified formulations with high levels of combustible solvents (high flash kerosene or bio-diesel).

Example 6

Treatment for Full Penetration of Pine Species

Individual slash pine samples of 90 mm×45 mm were treated with a vacuum process to achieve full penetration of wood preservative. Four formulations of bifenthrin containing 0.15% mass/volume active were used and the carriers varied as follows:
1. 100% High Flash Kerosene (HFK)
2. 66% High Flash Kerosene:34% water
3. 50% High Flash Kerosene:50% water
4. 34% High Flash Kerosene:66% water The process used involved flooding the timber with treatment formulation and placing at a negative pressure of −30 kPa for 2 minutes. The emulsion was then drained from the wood and a further negative pressure of −85 kPa was applied for 5 minutes.

The timber samples were weighed before and after treatment to assess uptake of formulation. The oil and water content was assessed by calculation based on the amount of oil and water in the formulation and initial moisture content.

Uptake results are shown in Table 6.

TABLE 6

| | Total uptake | Uptake of oil | Uptake of water | Moisture content increase |
|---|---|---|---|---|
| 100% HFK | 39.5 | 39.5 | 0 | 0 |
| 66% HFK 34% water | 29.1 | 19.2 | 9.6 | 2% |

TABLE 6-continued

| | Total uptake | Uptake of oil | Uptake of water | Moisture content increase |
|---|---|---|---|---|
| 50% HFK 50% Water | 30.2 | 15.1 | 15.1 | 3% |
| 34% HFK 66% Water | 25.8 | 8.5 | 17.0 | 3% |

The samples were then subject to analysis of bifenthrin retention in various zones of the wood. The wood samples were cut in cross-section and a sample at the cut wood was taken for analysis. A sample of timber at surface exposed to the treatment (5 mm) was taken for analysis. A sample of timber at >5 mm from the surface was taken (core) and a sample from the centre of the wood sample (central ninth) was taken for analysis.

Analysis was performed by extraction of the wood sample with acetone and analysis of the extract with gas chromatography (GC) to ascertain the mass % of bifenthrin in a given mass of wood.

Figure 1:
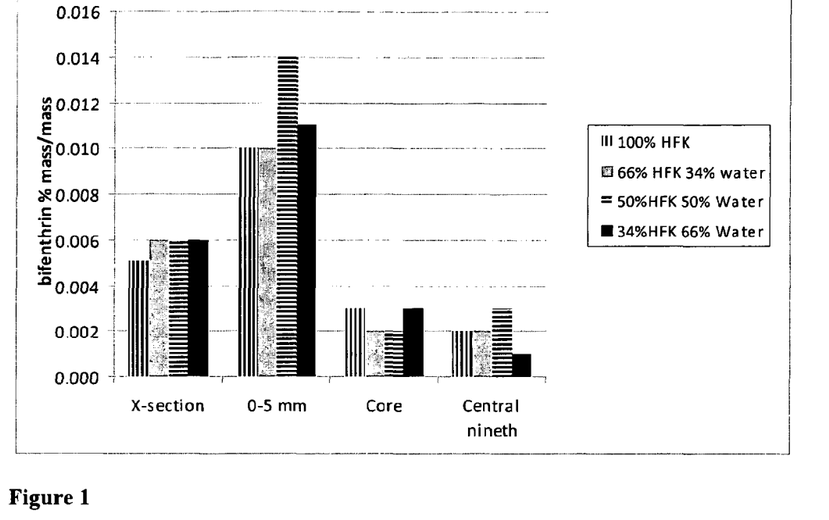
FIG. 1 is a graphical representation showing the bifenthrin retention (% mass of wood sample) from varying sites of treated wood, cross-section surface 0-5 mm, core and central ninth.

The results are shown in FIG. 1.

Surprisingly, retentions of bifenthrin in each zone analysed are almost the same irrespective of the ratio of oil to water. Advantageously, this reduces not only cost because less solvent is used, but also reduces the level of volatile organic compounds present and therefore odour associated with this process. There are also engineering advantages with this process as the emulsion is easier to deal with and has low flammability compared to LOSP processes. There was also minimal increase in moisture content and swelling of the treated wood and no loss of efficacy of the preservative as a result of using the emulsion carrier.

Example 7

Uptake and Penetration of Permethrin

Individual pieces of end sealed slash pine were dip treated in a formulation of 0.5% m/v permethrin in a carrier of 60 water:40 bio-diesel. The penetration of the permethrin was analysed by taking a 3 mm surface sample of wood and then a further 2 mm sample of wood from the new surface and extracting with acetone followed by analysis for permethrin content by GC.

Figure 2:
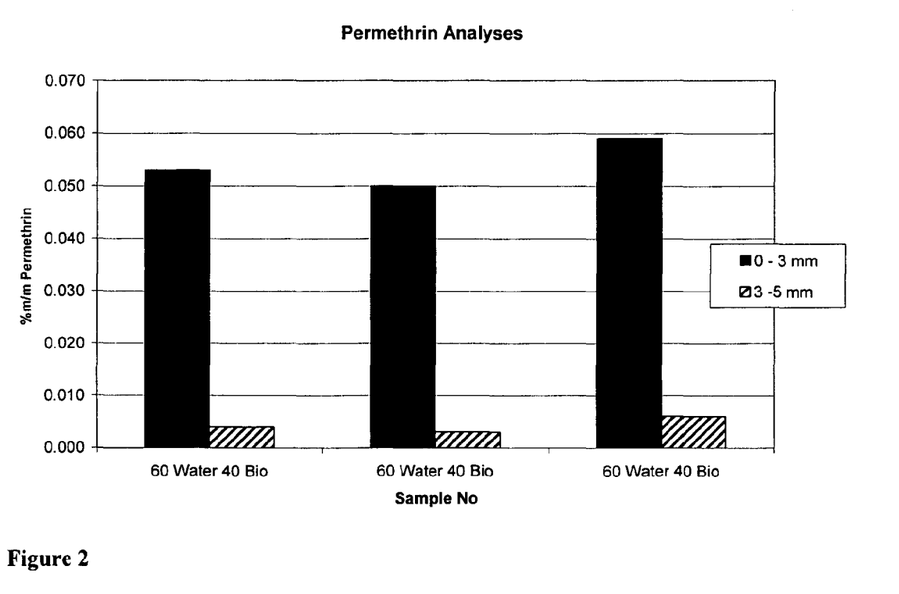
FIG. 2 is a graphical representation showing permethrin uptake at 0-3 mm and 3-5 mm using a carrier of 60:40 water:bio-diesel.

The results in triplicate are shown in FIG. 2.

Example 8

Uptake and Penetration of Bifenthrin

Individual pieces of end sealed slash pine were dip treated in a formulation of 0.5% m/v bifenthrin in a water:bio-diesel carrier having 60:40 water:bio-diesel, 80:20 water:bio-diesel and 90:10 water:bio-diesel.

The penetration of the bifenthrin was analysed by taking a 2 mm surface sample of wood and then subsequently a further 2 mm sample of wood from the new surface. The samples were extracted with acetone and analysed for bifenthrin content by GC.

Figure 3:
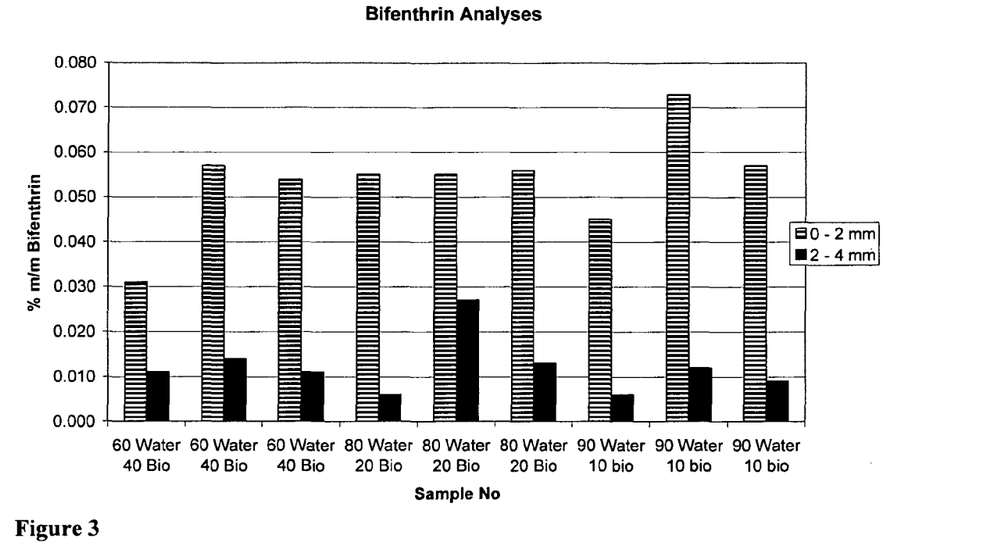
FIG. 3 is a graphical representation showing bifenthrin uptake at 0-2 mm and 2-4 mm using a carrier of 60:40, 80:20 or 90:10 water:bio-diesel.

The results are shown in FIG. 3.

Example 9

Timber Full Pack treatment

At least 6×4.8 meter slash pine full packs of varying piece size (70×35 mm and 90×45 mm) and grade were dipped in the experimental formulation. Dipping occurred at 5° angle for 60 seconds with pack leaving the dip at 5° angle but reverse to that used for initial submerging. The full pack was left on a drain angle of 33° for 8 minutes. Rate of flow from the pack was monitored to the point of no drip.

Prior to all treatments pack weights and individual board weights were taken. The position of each board in the pack was noted. After weighing, all boards were returned to their original position within the pack. The re-built packs were strapped as per standard practice and strap tension was the same as normally used.

The pack was re-weighed for calculation of uptake

After treatment the packs were broken and assessed for solution coverage i.e. presence of patches on the surface of the individual pieces.

The individual pieces were re-weighed to determine uptake.

Knowing the weight gain and position of individual boards allowed data to be collected to assess across pack variations in uptake and penetration.

The formulation used contained 0.5% mass/volume bifenthrin in a 80:20 water:bio-diesel emulsion.

Two size packs were analysed in the dip process, a 70×35 mm piece pack of slash pine containing 7×11 pieces of timber and a 90×45 mm piece pack of slash pine containing 5×9 pieces of timber.

The results are shown in Table 7 and 8.

TABLE 7

Uptake of formulation in L/m³ for each timber piece in a 70 × 35 mm piece pack
70 × 35 mm Uptakes

| 15.3 | 15.0 | 20.5 | 21.7 | 17.9 | 16.4 | 11.4 |
|------|------|------|------|------|------|------|
| 15.5 | 20.3 | 23.4 | 19.5 | 18.9 | 24.4 | 18.2 |
| 17.7 | 22.8 | 21.9 | 18.2 | 16.2 | 21.0 | 20.2 |
| 18.4 | 22.5 | 22.3 | 20.8 | 20.7 | 22.7 | 18.7 |
| 18.5 | 21.0 | 21.7 | 19.2 | 21.5 | 23.5 | 23.7 |
| 18.8 | 22.0 | 23.1 | 22.4 | 20.7 | 21.5 | 19.8 |
| 20.0 | 25.9 | 29.8 | 27.1 | 23.1 | 24.7 | 21.7 |
| 16.0 | 24.1 | 25.9 | 24.6 | 28.3 | 24.5 | 26.5 |
| 27.7 | 18.7 | 26.9 | 21.8 | 25.5 | 26.9 | 19.6 |
| 22.3 | 24.5 | 27.1 | 28.3 | 29.0 | 22.1 | 14.8 |
| 21.1 | 26.5 | 23.5 | 24.9 | 22.7 | 21.8 | 22.4 |

TABLE 8

Uptake of formulation in L/m³ for each timber piece in a 90 × 45 mm piece pack
90 × 45 mm Uptake

| 11.8 | 12.3 | 10.6 | 10.4 | 10.3 |
|------|------|------|------|------|
| 10.6 | 11.9 | 11.0 | 10.9 | 8.2  |
| 12.7 | 12.3 | 11.2 | 13.9 | 13.7 |
| 12.3 | 13.7 | 13.5 | 12.6 | 12.6 |
| 12.6 | 16.3 | 14.1 | 14.7 | 14.7 |
| 16.4 | 14.9 | 13.4 | 15.6 | 12.5 |
| 15.4 | 15.7 | 14.4 | 18.2 | 15.8 |
| 14.8 | 15.5 | 15.6 | 14.4 | 16.2 |
| 14.4 | 13.8 | 11.8 | 16.8 | 11.1 |

As can be seen by Tables 7 and 8, satisfactory penetration of the formulation was noted in all timber pieces, including the pieces in the centre of the pack.

Figure 4:
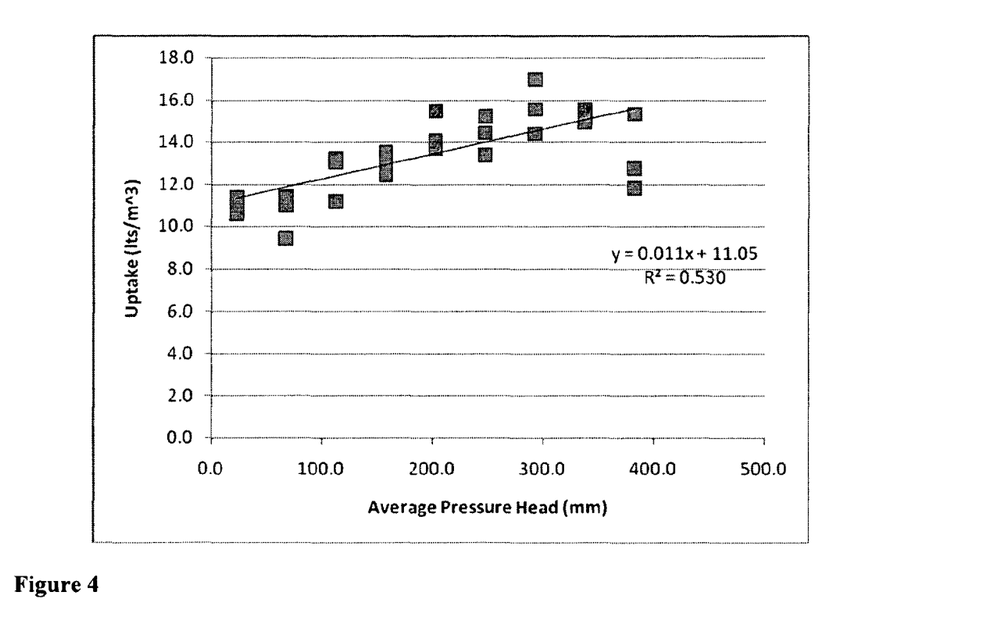
FIG. 4 is a graphical representation showing the effect of hydrostatic head pressure on uptake of formulation in a full pack of timber.

As can be seen by the uptake results the hydrostatic pressure or depth at which the timber piece is placed in the tank affects the levels of uptake. The timber pieces at the bottom of the pack placed at a lower level in the dip tank had a higher formulation uptake. The effect of hydrostatic head pressure on uptake of the formulation in a tightly strapped timber pack is shown in FIG. 4.

Where hydrostatic head pressure exceeded the pressure exerted by the strap tension, no patches were observed. A pressure differential (either positive or negative) of approximately 5 to 20 kPa is required depending on strap tension.

Example 10

Bifenthrin Uptake in Full Size Pack Treatment

Samples of timber from the full pack treatment in Example 9 were analysed for bifenthrin penetration. After treatment, timber samples of 0 to 2 mm, 2 to 4 mm and 4 to 5 mm from the surface of the treated wood sample were taken and extracted with acetone followed by GC analysis.

Figure 5:
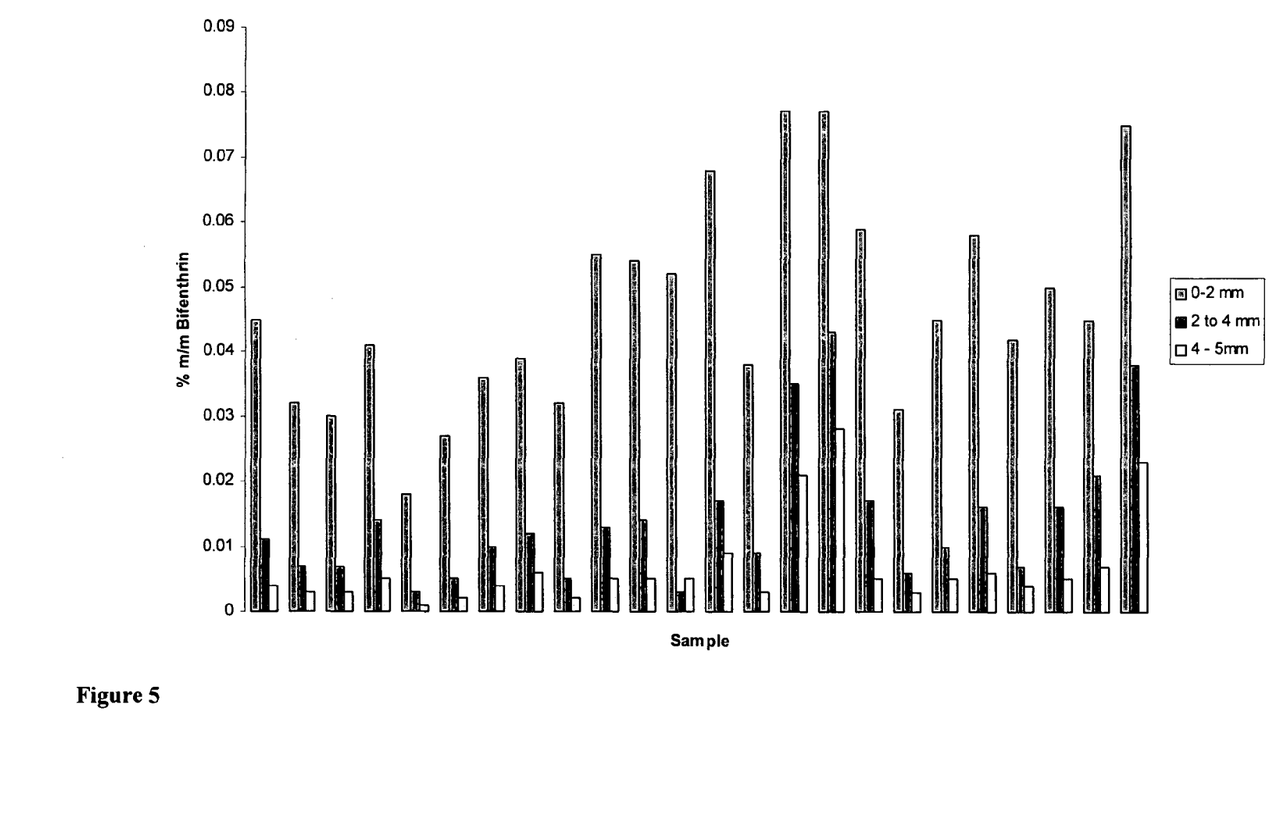
FIG. 5 is a graphical representation of bifenthrin loading (% mass/mass) in individual timber samples dipped as a full pack of timber.

The results for random samples throughout the pack are shown in FIG. 5.

Figure 6:
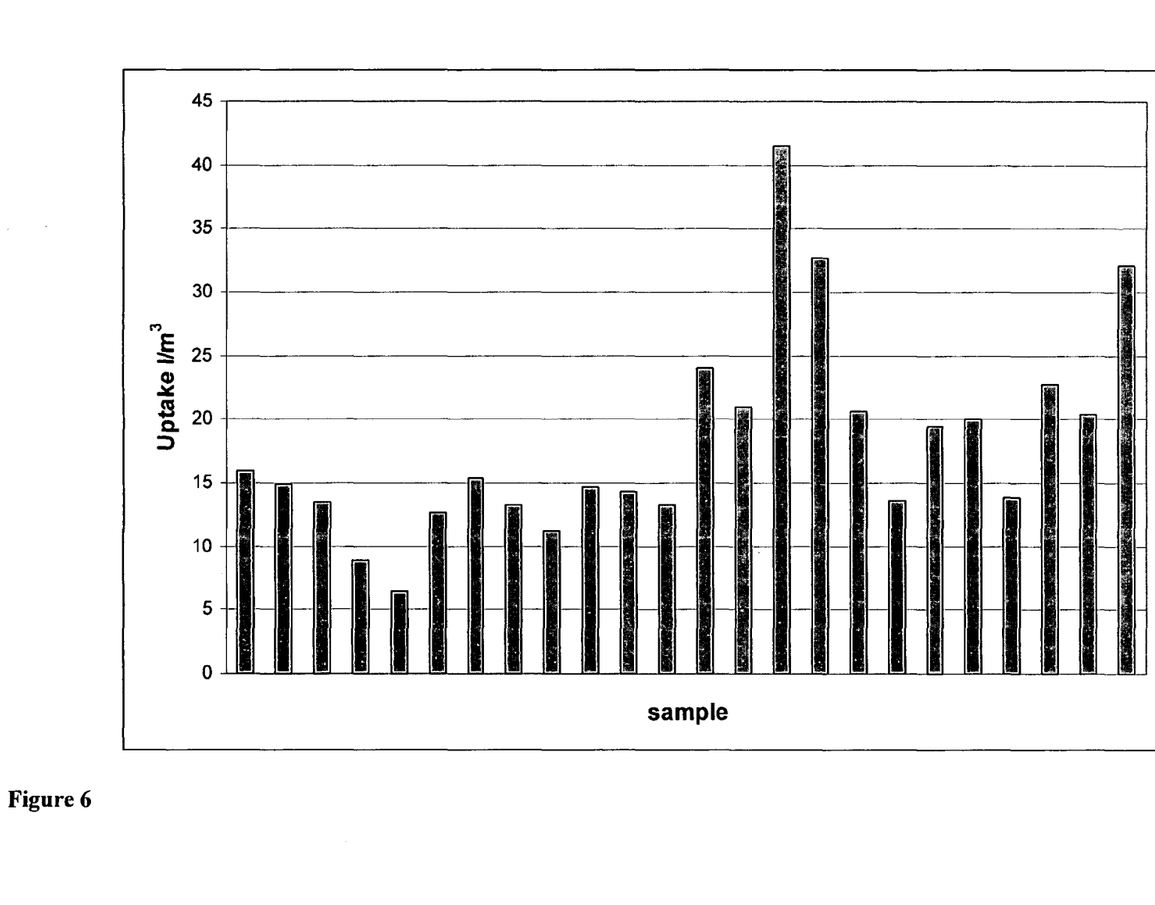
FIG. 6 is a graphical representation of the uptake of formulation in individual timber samples dipped as a full pack of timber.

The uptake of formulation was also analysed for each sample by assessment of weight before and after treatment. The results are shown in FIG. 6.

The results show that there is a trend of increasing loading due to increased uptake.

Example 11

Tightly strapped timber packs of pine timber were treated by immersion method in both a dip bath and in a vacuum pressure plant. All packs were strapped with three straps per pack.

Strap tension was assessed via tension meter calibrated to plastic strap being used.

Patches of non-coverage of the timber with the composition were assessed by breaking timber packs open and viewing individual layers. Individual timber pieces with patches greater than 50 mm wide and 100 mm in length that had no uptake of formulation were deemed to non-compliant (failed).

Pressure in dip bath is based on hydrostatic head pressure calculation. Hydrostatic head pressure was taken at top of pack.

Pressure in vacuum pressure plant was determined by pressure transducers fitted to the plant.

The results are shown in Table 9.

TABLE 9

| Method | Plant | Pack Size* | Strap Pressure (kg) | Immersion time (Seconds) | Pressure (kPa) | Patches | Result |
|--------|-------|-----------|---------------------|--------------------------|----------------|---------|--------|
| Immersion | Dip | 140 × 45 × 3.6 × 0.5 | 80 | 45 | 0 | Yes | Fail |
| Immersion | Dip | 140 × 45 × 3.6 × 0.5 | 80 | 45 | 10 | No | Pass |
| Immersion | Dip | 90 × 45 × 3.6 × 0.5 | 80 | 45 | 10 | No | Pass |
| Immersion | Dip | 90 × 45 × 3.6 × 0.5 | 80 | 20 | 10 | No | Pass |
| Immersion | Vac-Press | 140 × 45 × 3.6 × 0.5 | 130 | 45 | 0 | Yes | Fail |
| Immersion | Vac-Press | 140 × 45 × 3.6 × 0.5 | 130 | 20 | −15 | No | Pass |
| Immersion | Vac-Press | 140 × 45 × 3.6 × 0.5 | 130 | 20 | 11 | No | Pass |

*Size is width in millimetres by depth in millimetres by length in meters and height in meters The results show that positive or negative pressure exerted either by hydrostatic pressure in an immersion bath using the dip methods or using vacuum process can provide full coverage of the timber in a strapped pack and reduce patches of non-coverage to acceptable levels or remove them.

Example 12

Penetration of Bifenthrin into Pine Species

Example 6 was repeated and analysis of the bifenthrin loading was performed at the cross-section and core and at 0 to 5 mm, 0 to 7.5 mm or 0 to 10 mm.

Figure 7:
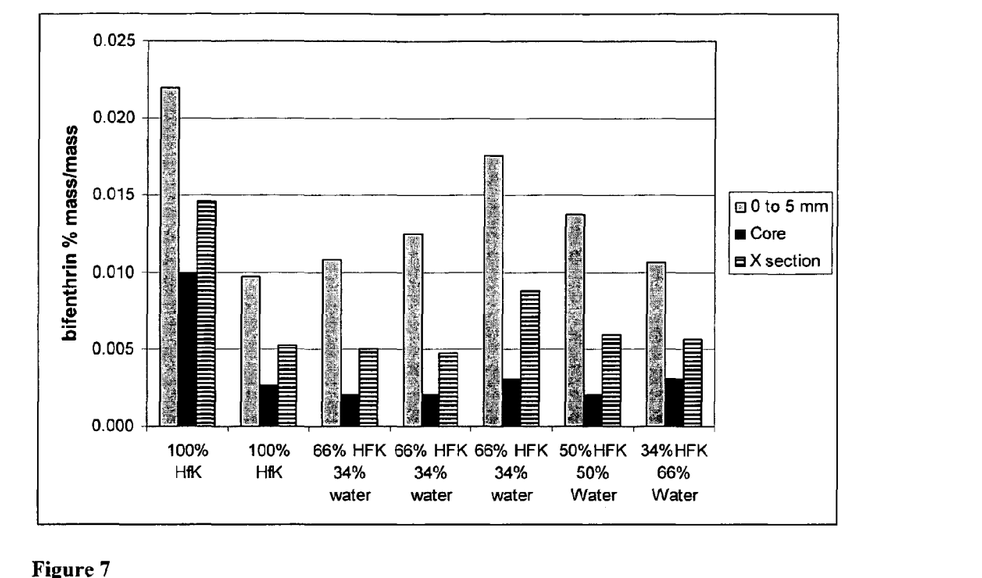
FIG. 7 is a graphical representation of the bifenthrin loadings (% mass/mass) in a cross-section, 0-5 mm and the remaining core after dip treatment.
Figure 8:
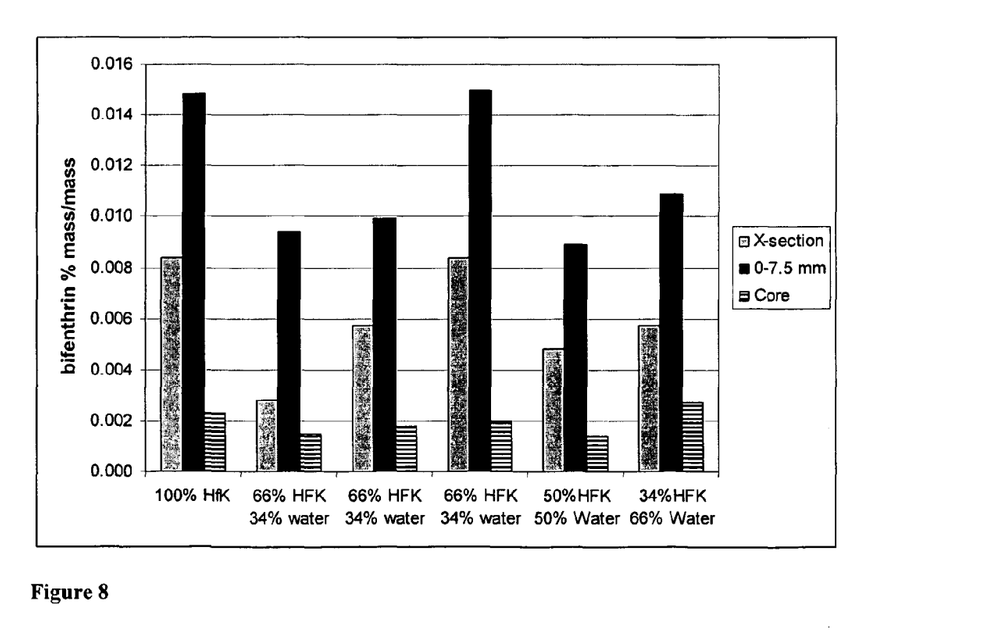
FIG. 8 is a graphical representation of the bifenthrin loadings (% mass/mass) in a cross-section, 0-7.5 mm and the remaining core after dip treatment.
Figure 9:
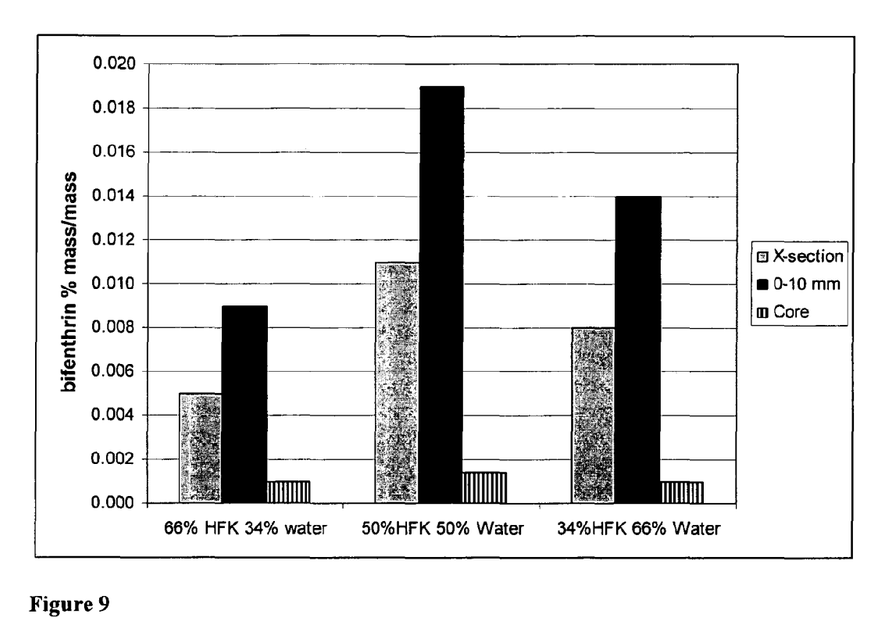
FIG. 9 is a graphical representation of the bifenthrin loadings (% mass/mass) in a cross-section, 0-10 mm and the remaining core after dip treatment.

The results are shown in Tables 10 and 11 and FIGS. 7 to 9.

TABLE 10

Uptake of formulation

| Formulation | Uptake HFK | Uptake water | Total uptake |
|---|---|---|---|
| 100% HFK | 46.5 | 0 | 46.5 |
| 100% HFK | 39.5 | 0 | 39.5 |
| 100% HFK | 28.2 | 0 | 28.2 |
| 66% HFK 34% water | 21.7 | 11.2 | 32.9 |
| 66% HFK 34% water | 27.6 | 14.2 | 41.8 |
| 66% HFK 34% water | 20.5 | 10.6 | 31.1 |
| 66% HFK 34% water | 19.2 | 9.9 | 29.1 |
| 66% HFK 34% water | 18.1 | 9.3 | 27.4 |
| 66% HFK 34% water | 20.6 | 10.6 | 31.3 |
| 66% HFK 34% water | 21.7 | 11.2 | 32.9 |
| 66% HFK 34% water | 18.0 | 9.3 | 27.3 |
| 50% HFK 50% Water | 15.1 | 15.1 | 30.2 |
| 50% HFK 50% Water | 12.7 | 12.7 | 25.4 |
| 50% HFK 50% Water | 13.7 | 13.7 | 27.4 |
| 34% HFK 66% Water | 8.5 | 17.3 | 25.8 |
| 34% HFK 66% Water | 11.1 | 22.5 | 33.6 |
| 34% HFK 66% Water | 8.6 | 17.5 | 26.2 |

TABLE 11

Comparison of bifenthrin penetration at different zones of timber

| | | | | | % m/m bifenthrin | | | |
| Formulation | Uptake HFK | Uptake water | Total uptake | X-section | 0-5 mm | 0-7.5 mm | 0-10 mm | Core |
|---|---|---|---|---|---|---|---|---|
| 100% HfK | 46.5 | 0 | 46.5 | 0.015 | 0.022 | | | 0.010 |
| 100% HfK | 39.5 | 0 | 39.5 | 0.005 | 0.010 | | | 0.003 |
| 100% HfK | 28.2 | 0 | 28.2 | 0.008 | | 0.015 | | 0.002 |
| 66% HFK 34% water | 21.7 | 11.2 | 32.9 | 0.005 | 0.011 | | | 0.002 |
| 66% HFK 34% water | 27.6 | 14.2 | 41.8 | 0.003 | | 0.009 | | 0.002 |
| 66% HFK 34% water | 20.5 | 10.6 | 31.1 | 0.005 | 0.013 | | | 0.002 |
| 66% HFK 34% water | 19.2 | 9.9 | 29.1 | 0.006 | | 0.010 | | 0.002 |
| 66% HFK 34% water | 18.1 | 9.3 | 27.4 | 0.005 | | | 0.009 | 0.001 |
| 66% HFK 34% water | 20.6 | 10.6 | 31.3 | 0.009 | 0.018 | | | 0.003 |
| 66% HFK 34% water | 21.7 | 11.2 | 32.9 | 0.008 | | 0.015 | | 0.002 |
| 66% HFK 34% water | 18.0 | 9.3 | 27.3 | 0.005 | | | 0.009 | 0.001 |
| 50% HFK 50% Water | 15.1 | 15.1 | 30.2 | 0.006 | 0.014 | | | 0.002 |
| 50% HFK 50% Water | 12.7 | 12.7 | 25.4 | 0.005 | | 0.009 | | 0.001 |
| 50% HFK 50% Water | 13.7 | 13.7 | 27.4 | 0.011 | | | 0.019 | 0.001 |
| 34% HFK 66% Water | 8.5 | 17.3 | 25.8 | 0.006 | 0.011 | | | 0.003 |
| 34% HFK 66% Water | 11.1 | 22.5 | 33.6 | 0.006 | | 0.011 | | 0.003 |
| 34% HFK 66% Water | 8.6 | 17.5 | 26.2 | 0.008 | | | 0.014 | 0.001 |

The invention claimed is:

1. A composition for treating wood comprising a carrier and at least one wood preserving compound; said carrier comprising an oil, water and a non-ionic surfactant and said carrier being an emulsion having a water to oil ratio:
    greater than 30 up to 92.5 water: 7.5 to less than 70 oil;
    wherein the oil has a flash point above 61° C.,
    and wherein said carrier is not a microemulsion.

2. A composition according to claim 1 wherein the ratio of water and oil in the emulsion is in the range of:
    greater than 30 up to 90 water: 10 to less than 70 oil.

3. A composition according to claim 1 wherein the ratio of water and oil in the emulsion is in the range of:
    45 to 80 water: 20 to 55 oil.

4. A composition according to claim 1 wherein the ratio of water and oil in the emulsion is in the range of:
    50 to 75 water: 25 to 50 oil.

5. A composition according to claim 1 wherein the oil is selected from mineral oils, vegetable oils, aromatic solvents or oils and biodiesel or mixtures thereof.

6. A composition according to claim 5 wherein the oil is isoparaffin, narrow cut kerosene, high flash kerosene or biodiesel sourced from non-edible vegetable oils.

7. A composition according to claim 1 wherein the at least one wood preserving compound is selected from synthetic pyrethroids, metal naphthenates, copper, silver and zinc compounds, organic tin compounds, quaternary ammonium compounds, tertiary ammonium compounds, isothiazalones, boron compounds, neonicotinoid compounds, azoles, pentachlorophenol and creosote or mixtures thereof.

8. A composition according to claim 7 wherein the at least one wood preserving compound is selected from synthetic pyrethroids, neonicotinoid compounds and azoles or mixtures thereof.

9. A composition according to claim 8 wherein the synthetic pyrethroid is selected from bifenthrin or permethrin.

10. A composition according to claim 8 wherein the neonicotinoid compound is selected from imidichloprid and thiochloprid.

11. A composition according to claim 8 wherein the azole is selected from propiconizole and tebuconizole or mixtures thereof.

12. A composition according to claim 8 wherein the at least one wood preserving compound is a mixture of propiconizole, tebuconizole and permethrin or bifenthrin.

13. A composition according to claim 1 wherein the non-ionic surfactant has an HLB of between 4 and 12.

14. A method of treating wood comprising the steps of:
    providing wood for treatment, wherein the wood is timber or an engineered wood product;
    contacting the wood to a composition of claim 1.

15. A method according to claim 14 wherein the wood is contacted with the composition by dipping, spraying, rolling, misting or brushing.

16. A method according to claim 15 wherein the wood is a strapped pack and is contacted with the composition by dipping.

17. A method according to claim 16 wherein the dipping method applies a hydrostatic head pressure of at least 5 kPa at the top of the strapped pack.

18. A method according to claim 14 wherein the wood is contacted with the composition in a vacuum pressure process.

19. Wood treated by the method of claim 14.

20. A method according to claim 14 wherein the treatment allows penetration of preservatives without substantially increasing the moisture content of the wood.

* * * * *